United States Patent
Akins et al.

(10) Patent No.: US 6,676,841 B2
(45) Date of Patent: Jan. 13, 2004

(54) WATER-IN-FUEL ABUSE DETECTION

(75) Inventors: Mark Akins, Columbus, IN (US); Scott Thompson, Columbus, IN (US); Gopal Chamarthi, Farmington Hills, MI (US); Stephanie Goerges, Franklin, IN (US)

(73) Assignee: Cummins Inc., Columbus, IN (US)

( * ) Notice: Subject to any disclaimer, the term of this patent is extended or adjusted under 35 U.S.C. 154(b) by 0 days.

(21) Appl. No.: 09/992,143

(22) Filed: Nov. 6, 2001

(65) Prior Publication Data

US 2003/0085180 A1 May 8, 2003

(51) Int. Cl.$^7$ .............................................. B01D 35/143
(52) U.S. Cl. ........................ 210/744; 210/86; 340/439; 340/450; 701/29; 701/35; 705/4
(58) Field of Search .............................. 210/85, 86, 90, 210/94, 103, 143, 171, 172, 739, 744, 767, 138; 705/1, 4; 340/290 R, 304 C, 438, 439, 450, 459, 461; 701/29, 30, 35; 702/55

(56) References Cited

U.S. PATENT DOCUMENTS

| | | |
|---|---|---|
| 3,824,823 A | 7/1974 | Pontello |
| 4,227,173 A | 10/1980 | Clark |
| 4,488,970 A | 12/1984 | Clark |
| 5,534,161 A * | 7/1996 | Tarr et al. .................... 210/744 |
| 5,613,398 A | 3/1997 | Lawson |
| 5,626,052 A | 5/1997 | Lawson |
| 5,754,055 A | 5/1998 | McAdoo et al. |
| 5,824,889 A | 10/1998 | Park et al. |
| 5,880,674 A * | 3/1999 | Ufkes et al. ................. 340/438 |
| 5,889,200 A | 3/1999 | Centers et al. |
| 6,151,956 A | 11/2000 | Takahashi et al. |
| 6,172,602 B1 * | 1/2001 | Hasfjord ..................... 340/438 |
| 6,268,913 B1 | 7/2001 | Rising |
| 6,463,967 B1 * | 10/2002 | Boyle |

* cited by examiner

*Primary Examiner*—Joseph Drodge
(74) *Attorney, Agent, or Firm*—Woodard, Emhardt, Moriarty, McNett & Henry, LLP

(57) ABSTRACT

A water-in-fuel abuse detection system provides a way to determine if a vehicle operator has ignored a conventional water-in-fuel indicator light and continued to operate the vehicle beyond a certain threshold. The system includes a sensor positioned in a fuel filter capable of separating an amount of water from a source of fuel. The sensor is operatively connected to a software routine, as well as to a conventional indicator light that illuminates to alert a vehicle operator that water must be purged from the fuel filtration system. The software routine determines the duration, in distance traversed or time elapsed, that the amount of water is at or above the level of the sensor. The routine then writes a fault code to permanent memory when the threshold is exceeded. A diagnostic tool can access the permanent memory and reveal whether the fuel system has be the subject of water-in-fuel abuse.

18 Claims, 5 Drawing Sheets

WATER-IN-FUEL ABUSE DETECTION

The present invention relates to fuel systems, and more specifically to fuel systems, such as diesel fuel systems, that separate, monitor, and require disposal of water that accumulates therein.

BACKGROUND OF THE INVENTION

Water accumulates in fuel storage tanks, as well as in the fuel tanks on vehicles such as cars, trucks, buses, boats, construction equipment and on other mobile and stationary engines. The presence of water in fuel tanks can be attributed to a variety of causes, such as ground water seepage, rain water collection, and condensation of water from air.

Engine fuel systems, particularly diesel fuel systems, include a fuel filtration system for separating the water from the fuel. The fuel filtration system may also include a way to monitor how much water has been collected so that the water can be periodically purged by, for example, opening a drain valve. A vehicle operator is alerted to the need to drain the water collected by the fuel filtration system by the illumination of a warning light on the dashboard of the vehicle.

If a vehicle operator ignores the warning light and fails to periodically purge the fuel filtration system of water, then the water backs-up and eventually overflows into the fuel system of the engine. If the engine continues to run allowing water to run through the fuel system, rust builds up and eventually leads to internal engine damage.

Warranty claims are often made on failed fuel injection pumps. Only after payment of such a claim, does a pump supplier remove the fuel injection pump, tear it down, and then discover internal rusting. Thus, the need exists for a way to detect fuel-in-water abuse without disassembly of the engine. The present invention meets this need in a novel and unobvious way.

SUMMARY OF THE INVENTION

The present invention utilizes a software program and a water sensor in the vehicle's fuel filtration system to monitor if the vehicle operator ignores the conventional dashboard warning light and continues to operate the engine when water is present in the fuel filtration system. In one embodiment of the present invention, the program detects chronic abuse by calculating the total duration of vehicle operation while the water-in-fuel dashboard warning light is illuminated. The duration of abuse can be calculated in terms of either distance traversed or time elapsed. In an alternative embodiment, the program records single-event abuse which occurs when the operator neglects the water-in-fuel warning light for one extended period of time.

A distance or time threshold is chosen, and, once exceeded, the software program writes a permanent fault code to the engine control memory. A diagnostic tool applied to the engine control memory is capable of reading the fault code stored therein. The absence of the fault code permits an engine manufacturer to conclude that warranty coverage is justified; whereas, the presence of the fault code reveals that the vehicle operator ignored the water-in-fuel indicator and neglected to purge the water from the fuel filtration system. The fault code permanently remains in the engine control memory in order to retain a history of engine abuse in the event of changes in vehicle ownership.

One feature of the present invention is a system for detecting water-in-fuel abuse that includes a fuel filter, a means for detecting if water located therein reaches a certain level, and means for determining the duration that water is detected at or above that level. The system may also include means for recording if the duration exceeds a threshold.

Another feature of the present invention is a method for detecting water-in-fuel abuse that includes providing a fuel filter, detecting if the water level in the filter reaches a certain level, and calculating the duration that the water level is at or above that level. The method may additionally include writing a fault code to permanent memory if the duration exceeds a threshold.

Another form of the present invention uses the software program to count the number of events of water-in-fuel abuse (i.e., the number of times that the water-in-fuel dashboard warning light has been illuminated). A still further form of the present invention determines the longest duration of any single event of water-in-fuel abuse. These data may be written to permanent memory. A diagnostic tool is capable of accessing these data stored in permanent memory.

Accordingly, one object of the present invention is to provide a unique way of detecting fuel-in-water abuse.

Related objects and advantages of the present invention will be apparent from the following description.

DESCRIPTION OF THE PREFERRED EMBODIMENTS

Figure 1:
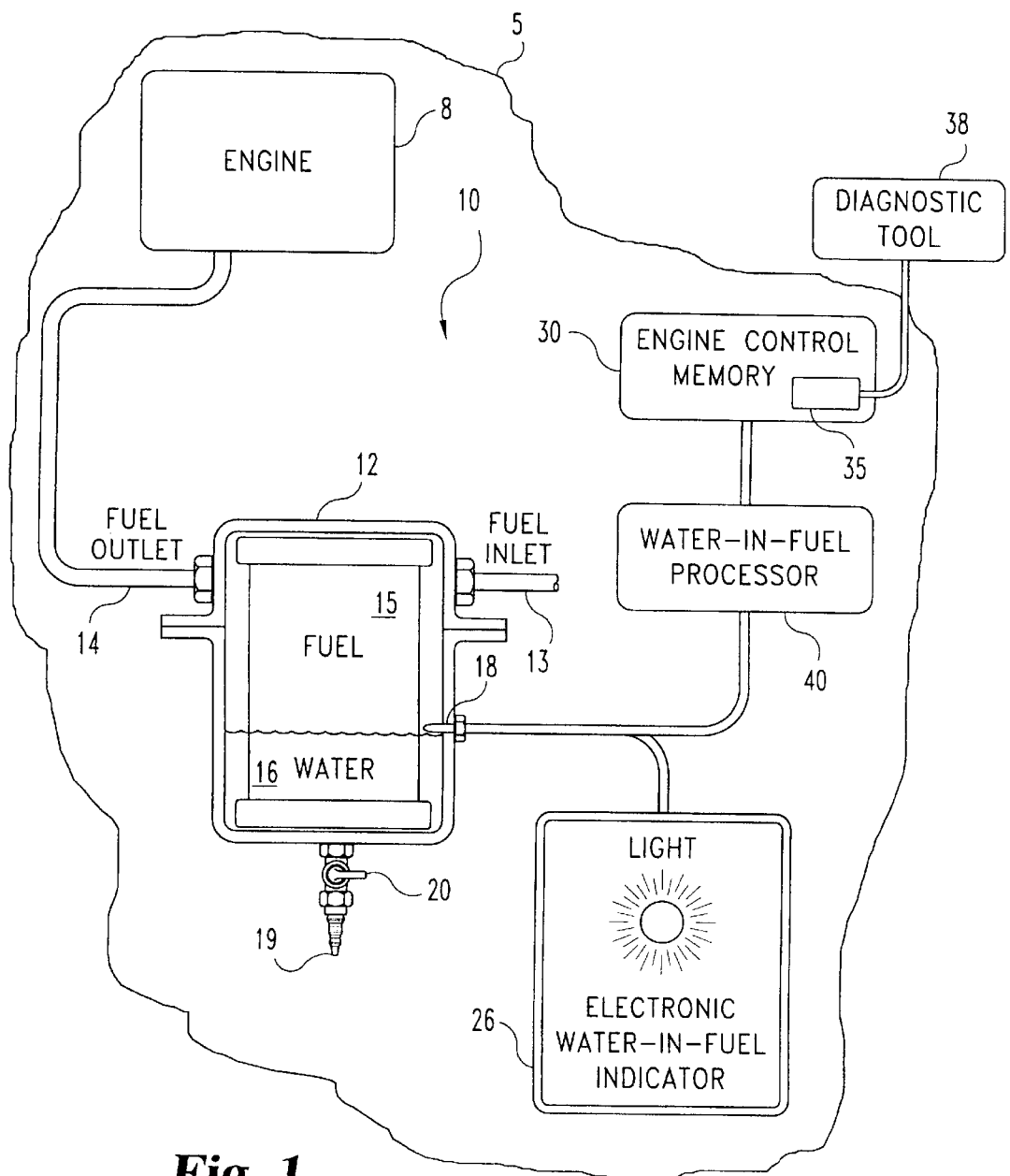
FIG. 1 is a schematic view of one embodiment of the present invention.

For the purpose of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

With reference to FIG. 1, there is illustrated ground vehicle 5, such as a car, truck, or bus, propelled by diesel fuel. Although diesel fuel is specified herein, the present invention includes any type of automotive engine fuel within its scope. Ground vehicle 5 includes a fuel filtration system that contains one embodiment of water-in-fuel abuse detection system 10 according to the present invention. Water-in-fuel abuse detection system 10 includes fuel filter 12, means 18 for detecting the presence of water therein, and processing means 40. A source of fuel, possibly contaminated with water, enters fuel filter 12 through fuel inlet 13. Fuel filter 12 separates water 16 from fuel 15 which then exits fuel filter 12 through fuel outlet 14. Fuel outlet 14 is connected to engine 8 of ground vehicle 5.

Means for detecting the presence of water, such as sensor 18, is positioned in fuel filter 12 at a certain level. Sensor 18 could be a pair of electrodes that conduct electricity when water rises to the level of the sensor, thereby completing an electrical circuit therebetween. Various means of water detection are contemplated by the present invention and will not be discussed in further detail as they are believed to be well known to those of ordinary skill in the art.

Water-in-fuel processor 40 is operatively connected to sensor 18 such that the output of sensor 18 (either the presence or absence of water 16 at the sensor level) is communicated to water-in-fuel processor 40. The location of sensor 18 in fuel filter 12 is selected such that an amount of water sufficient to trigger sensor 18 warrants notifying the vehicle operator to purge fuel filter 12 of water 16. A vehicle operator opens valve 20 to purge water 16 from fuel filter 12 through drain 19 and then closes valve 20 to permit the continued operation of fuel filter 12. Sensor 18 is operatively connected to electronic water-in-fuel indicator 26 located generally on the dashboard of vehicle 5. When the amount of water 16 in fuel filter 12 attains a quantity such that sensor 18 detects the presence of water, the light of electronic water-in-fuel indicator 26 illuminates, thereby notifying the vehicle operator of the need to purge water 16 from fuel filter 12. Power connections to illuminate indicator 26 are not shown.

In a preferred embodiment, water-in-fuel abuse detection system 10 also includes permanent memory means 35 within engine control memory 30 of vehicle 5. Permanent memory means 35 is accessed via operative connection to water-in-fuel processor 40. Water-in-fuel processor 40 contains a software routine to monitor if the vehicle operator ignores indicator 26 and continues to operate the vehicle allowing water 16 to exit fuel filter 12 through outlet 14 instead of being properly purged through drain 19.

Figure 2:
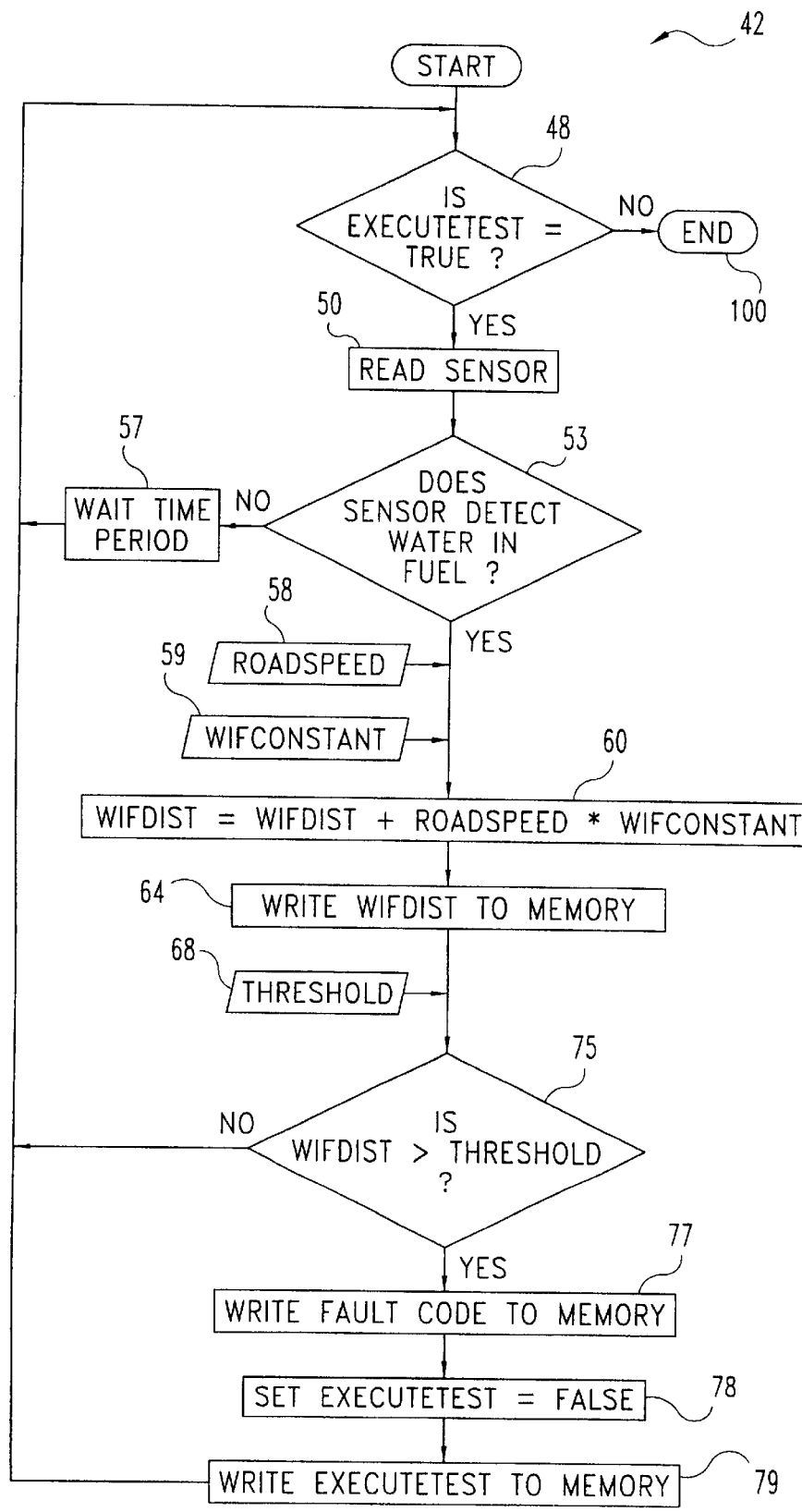
FIG. 2 is a flowchart of one embodiment of software capable of detecting chronic water-in-fuel abuse and suitable for execution in accordance with the present invention.

One embodiment of the software in processor 40 is routine 42, illustrated in FIG. 2, which begins with query 48 whether to execute the test to determine if the vehicle operator is ignoring indicator 26. The logic variable EXECUTETEST is initially set to TRUE. If EXECUTETEST is TRUE, sensor 18 is read at stage 50; however, if EXECUTETEST is FALSE, routine 42 ends at stage 100. If EXECUTETEST is TRUE and the water-in-fuel test is being performed, routine 42 proceeds to query 53 where it asks whether sensor 18 detects water. If water 16 has not attained a quantity sufficient to trigger sensor 18, the answer to query 53 is NO, and routine 42 is instructed to wait for some period of time at stage 57 before returning to the start.

If sensor 18 detects the presence of water, the answer to query 53 is YES, and the road speed (ROADSPEED) of the vehicle and a constant (WIFCONSTANT) are input at stages 58 and 59, respectively. The duration of water-in-fuel abuse is computed at stage 60. The duration of water-in-fuel abuse can be calculated in terms of either distance traversed or time elapsed. For illustrative purposes, FIG. 2 depicts calculation of the duration of water-in-fuel abuse in terms of distance.

A quantity sufficient to trigger sensor 18 denotes the distance traversed by vehicle 5 while the amount of water 16 equals or exceeds WIFDIST. The value of WIFDIST is initially set to 0.0. At stage 60, WIFDIST, is updated according to WIFDIST=WIFDIST+ROADSPEED*WIFCONSTANT, where WIFCONSTANT is a scaling factor to convert speed to distance based on the execution rate of routine 42. The new value of WIFDIST is written to memory at stage 64. If the distance calculated at stage 60 does not exceed a threshold distance, THRESHOLD, input at stage 68, the answer to query 75 is NO and routine 42 returns to the start to continue updating WIFDIST. If, however, WIFDIST exceeds THRESHOLD at query 75, the vehicle operator has ignored water-in-fuel indicator 26 too long and routine 42 implements a means for recording the abuse. A fault code is written to permanent memory means 35 at stage 77. Note that if the duration of water-in-fuel abuse is calculated in terms of time, THRESHOLD will be a time value. Continued execution of software routine 42 is no longer necessary if the duration of water-in-fuel abuse has exceeded the threshold; thus, EXECUTETEST is set to FALSE at stage 78 and written to memory at stage 79, before returning to the start. Of course, stages 77 and 78 may be executed in either order. At engine powerdown, the values of EXECUTETEST and WIFDIST are stored and retained in engine control memory 30. Once EXECUTETEST is set to FALSE, the water-in-fuel test is not performed again, unless and until the engine manufacturer resets EXECUTETEST to TRUE upon rebuilding, repairing, or replacing the engine fuel system, or some portion thereof.

An alternative response to a NO answer to query 53 is to end software routine 42. This alternative response results in performing the water-in-fuel test only once upon start-up of the engine. If no water is detected by sensor 18 at engine start-up, then software routine 42 ends and is not performed again until the engine is restarted. Returning to the start of routine 42 to re-test after waiting at stage 57, as illustrated in FIG. 2, enables routine 42 to calculate any water-in-fuel abuse that occurs subsequent to start-up of the engine.

A person of ordinary skill in the art would appreciate that electronic water-in-fuel indicator 26 may fail to illuminate despite the detection of water by sensor 18. This failure may be caused by any number of problems, such as an electrical short or indicator light burn-out. Thus, verification of the illumination of water-in-fuel indicator 26 may be added to routine 42. Alternatively, a separate value of the duration of water-in-fuel abuse could be calculated based on the duration of illumination of indicator 26 and then compared to that calculated based on the reading from sensor 18.

Figure 3:
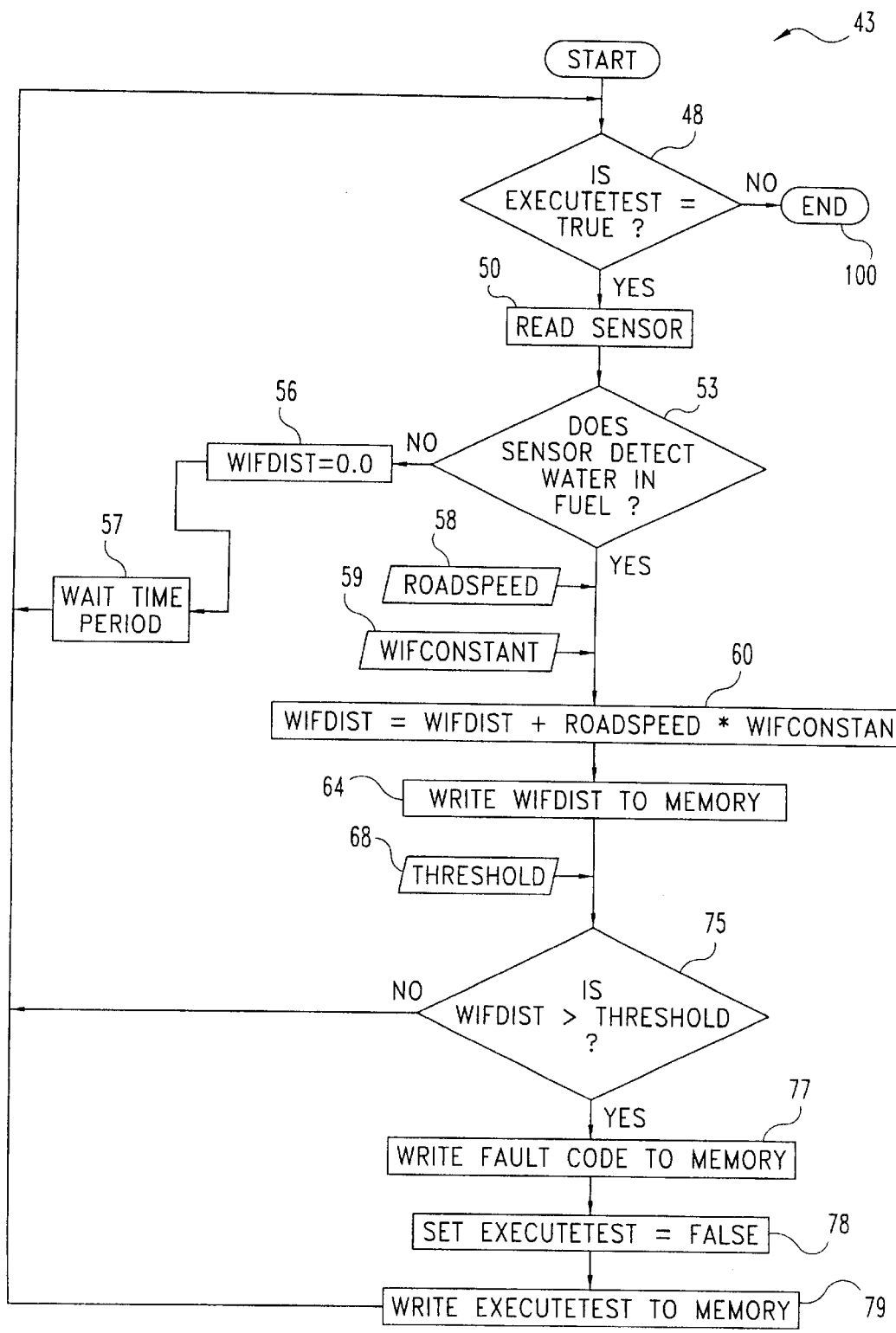
FIG. 3 is a flowchart of one embodiment of software capable of detecting single-event water-in-fuel abuse and suitable for execution in accordance with the present invention.

Software routine 42 enables an engine manufacturer to detect chronic water-in-fuel abuse, that is, numerous instances of abuse that tallied together exceed THRESHOLD. A further alternative embodiment of software routine 42 is routine 43 illustrated in FIG. 3. Software routine 43 enables the detection of single-event water-in-fuel abuse. FIG. 3 is identical to FIG. 2 with the exception of the process following a NO answer to query 53. If no water is detected at query 53, routine 43 sets WIFDIST=0.0 at stage 56 before returning to the start. Of course, stage 56 may be followed by waiting for some period of time at stage 57. Alternatively, as discussed above, routine 43 may simply end after stage 56 to enable water-in-fuel abuse detection upon engine start-up only. Setting WIFDIST=0.0 if no water is detected causes the fault code to be written to permanent memory only if a single instance of abuse rises to exceed the threshold input at stage 68. Of course, the value of the single-event abuse threshold in routine 43 can, and most likely will, be different from the chronic abuse threshold in routine 42. Software routine 43 can be implemented in place of, or in conjunction with, routine 42.

Figure 4:
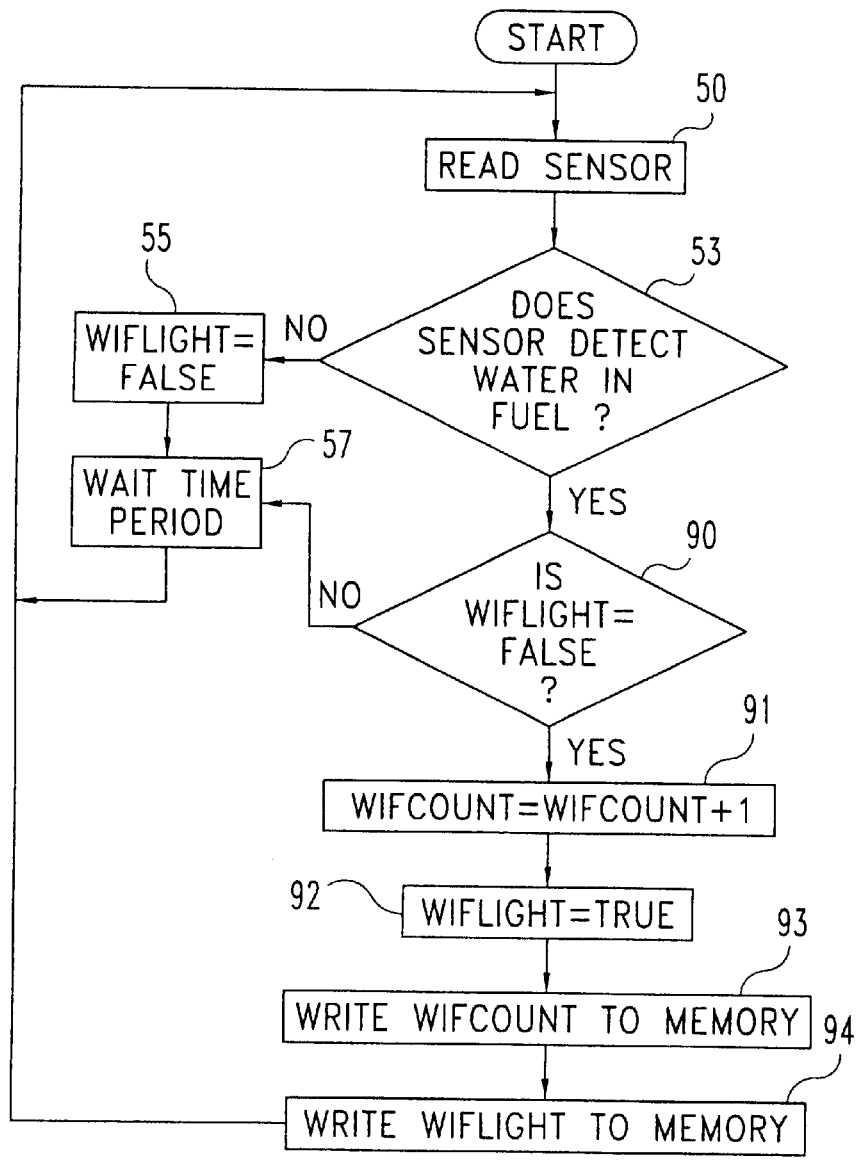
FIG. 4 is a flow chart of one embodiment of software capable of counting the number of events of water-in-fuel abuse and suitable for execution in accordance with the present invention.
Figure 5:
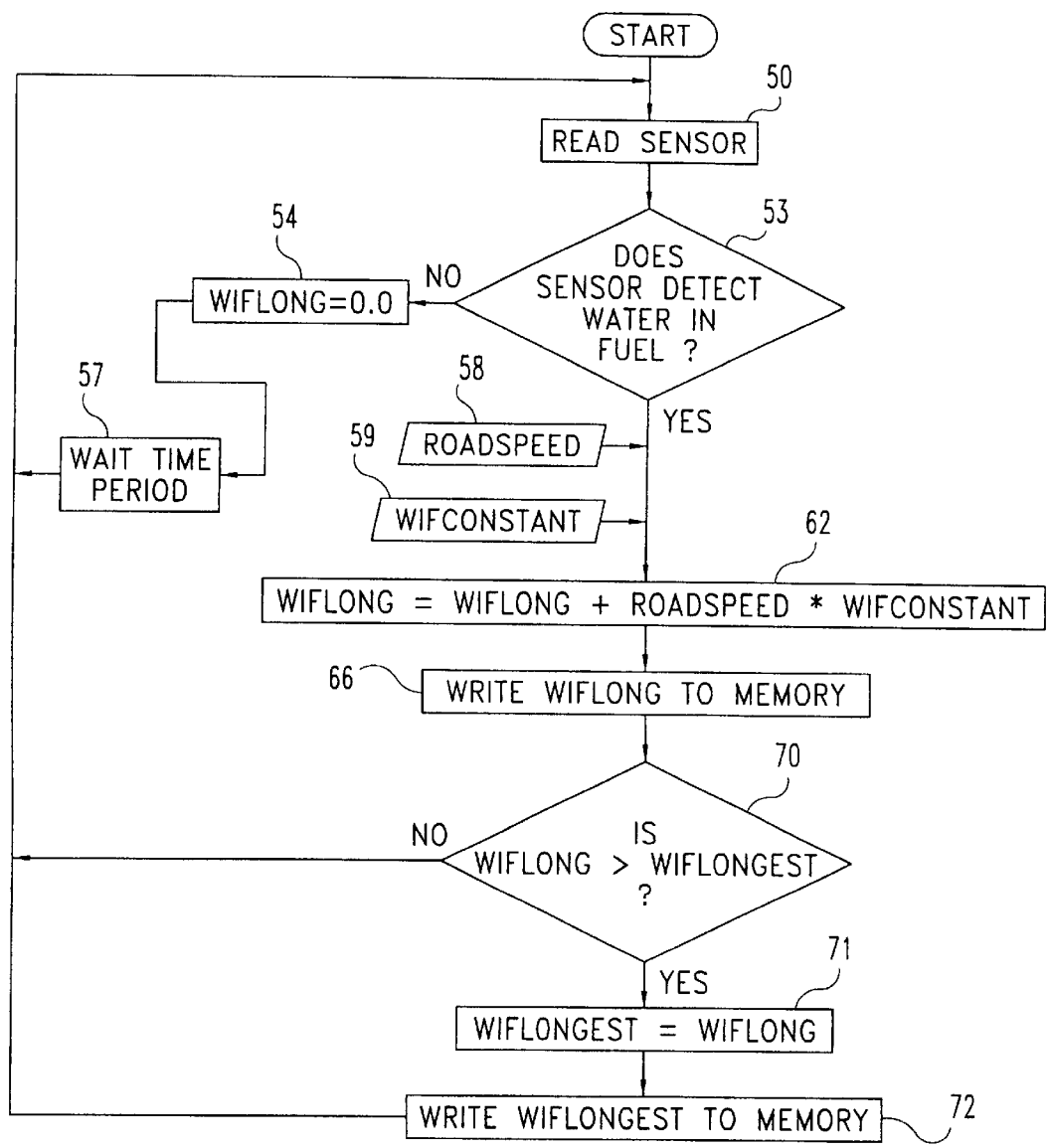
FIG. 5 is a flow chart of one embodiment of software capable of determining the longest duration of any single event of water-in-fuel abuse and suitable for execution in accordance with the present invention.

Engine manufacturers may be interested in obtaining water-in-fuel data in addition to whether the duration of water-in-fuel abuse (either chronic or single event) has exceeded a given threshold. An historical chronology of water-in-fuel abuse in terms of distance traversed while indicator 26 is illuminated can be created by writing the value of WIFDIST to an array stored in permanent memory means 35 at stage 64 of routines 42 or 43. Moreover, data such as the number of events of water-in-fuel abuse (i.e., the number of times that the quantity of water 16 in fuel filter 12 is sufficient to trigger sensor 18, thereby causing electronic water-in-fuel indicator 26 to illuminate), as well as the longest duration of any single event of water-in-fuel abuse are helpful in determining the appropriate value to assign to THRESHOLD at stage 68. FIGS. 4 and 5 illustrate software routines that provide these data. Note that the same reference numerals are used in FIGS. 4 and 5 to indicate stages or queries identical to those found in routines 42 and 43.

FIG. 4 illustrates one embodiment of a software routine that counts the discreet number of events of water-in-fuel abuse. Such an event is characterized by sensor 18 detecting that the amount of water 16 in fuel filter 12 equals or exceeds a certain quantity. The logic variable WIFLIGHT is initially set to FALSE, and the integer variable WIFCOUNT is initially set to zero. Routine 44 begins by reading sensor 18 at stage 50 and then posing query 53. If water 16 has not attained a quantity sufficient to trigger sensor 18, the answer to query 53 is NO, logic variable WIFLIGHT is set to FALSE at stage 55, and routine 44 is instructed to wait for some period of time at stage 57 before returning to the start. An alternative response to a NO answer to query 53 is, as discussed above, to end routine 44 after stage 55, thereby updating counter WIFCOUNT upon engine start-up only.

If sensor 18 detects the presence of water, the answer to query 53 is YES. Routine 44 then proceeds to query 90 where it asks whether logic variable WIFLIGHT is FALSE. If WIFLIGHT is not FALSE, routine 44 proceeds to stage 57 where it waits before returning to the start. But, if WIFLIGHT is FALSE, the integer counter WIFCOUNT is increased by one at stage 91 and WIFLIGHT is set to TRUE at stage 92. The values of WIFCOUNT and WIFLIGHT are then written to permanent memory means 35 at stages 93 and 94, respectively. An alternative embodiment of routine 44 includes the input of a threshold that, when exceeded by WIFCOUNT, triggers the writing of a fault code to permanent memory means 35 as illustrated by routines 42 and 43 in FIGS. 2 and 3, respectively.

The purpose of logic variable WIFLIGHT is to allow WIFCOUNT to advance one unit and thereby record an event of water-in-fuel abuse only after fuel filter 12 has been in a nominal state. Fuel filter 12 exists in a nominal state when new and initially placed in vehicle 5. Fuel filter 12 also returns to a nominal state after it has been purged of water such that sensor 18 does not detect the presence of water therein. The significance of WIFLIGHT being FALSE is that immediately prior to the detection of water by sensor 18 at query 53, the light of water-in-fuel indicator 26 was off. To achieve an accurate count of water-in-fuel events, even if that event spans over one or more engine start-ups, WIFCOUNT is increased only if sensor 18 detects water subsequent to fuel filter 12 existing in a nominal state immediately prior to queries 53 and 90. Further, WIFLIGHT is set to TRUE after the counter WIFCOUNT has recorded the event. WIFLIGHT is not reset to FALSE to allow the counter to advance until stage 55 after a NO answer to query 53. Without query 90 to test whether logic variable WIFLIGHT is FALSE, counter WIFCOUNT would be advanced incrementally each time routine 44 commenced and sensor 18 detected water. In this way, a single water-in-fuel event spanning one or more engine start-ups would be counted multiple times. Of course, if knowledge of the number of times water-in-fuel indicator 26 is illuminated at engine start-up is desired, routine 44 could be modified to run only once at engine start-ups and to provide a counter for each time the answer to query 53 is YES.

With reference to FIG. 5, one embodiment of a software routine to determine the longest duration of any single event of water-in-fuel abuse is illustrated. The values of variables WIFLONG and WIFLONGEST are both initially set to 0.0. Routine 45 begins by reading sensor 18 at stage 50 and then posing query 53. If water 16 has not attained a quantity sufficient to trigger sensor 18, the answer to query 53 is NO, the value of WIFLONG is set to 0.0 at stage 54, and routine 45 is instructed to wait some period of time at stage 57 before returning to the start. Alternatively, as discussed above, routine 45 may end after stage 54 to enable water-in-fuel abuse detection at engine start-up only.

If sensor 18 detects the presence of water, the answer to query 53 is YES, and the roadspeed of the vehicle and a constant are input at stages 58 and 59, respectively. The duration of water-in-fuel abuse is computed at stage 62. As noted with respect to routine 42 in FIG. 2, the duration of water-in-fuel abuse can be calculated in terms of either distance traversed or time elapsed.

WIFLONG is the distance traversed by vehicle 5 while the amount of water 16 equals or exceeds the quantity sufficient to trigger sensor 18. At stage 62, WIFLONG is updated according to WIFLONG=WIFLONG+ROADSPEED*WIFCONSTANT, where WIFCONSTANT is a scaling factor to convert speed to distance based upon the execution rate of routine 45. The new value of WIFLONG is written to memory at stage 66. If the distance calculated at stage 62 does not exceed the value of the variable WIFLONGEST, the answer to query 70 is NO and routine 45 returns to the start to continue updating WIFLONG. WIFLONGEST is the greatest value recorded for the duration of a single event of water-in-fuel abuse occurring prior to the computation at stage 62. Thus, if the value of WIFLONG exceeds WIFLONGEST, the answer to query 70 is YES and a new value is assigned to WIFLONGEST at stage 71. The new value of WIFLONGEST is written to permanent memory means 35 at stage 72 before routine 45 returns to the start to continue updating WIFLONG. Note that if the vehicle operator purges fuel filter 12 of water 16 so that the answer to query 53 is NO, the value of WIFLONG is re-initialized to 0.0 at stage 54.

Software routines 42, 43, 44 and 45 can be executed individually, or in conjunction with one another. When more than one of the routines 42–45 are to be implemented, the routines may be executed separately as subroutines, or they may be combined into one software routine. The later option would shorten processing time give the similarity in routines 42–45. Note, however, that whenever routine 44 or 45 is combined with routine 42 or 43, query 48 in routines 42 and 43 should be eliminated since routines 44 and 45 must be executed throughout the duration of vehicle operation and are not terminated upon the attainment of a given threshold.

The choice of which routines to implement is informed by the type of information that the engine manufacturer wants to obtain at the time of application of diagnostic tool 38 to permanent memory means 35. For example, if, upon diagnosis, the engine manufacturer wants to learn how many events of water-in-fuel abuse had occurred thus far, as well as whether the operator of vehicle 5 had ever traversed in excess of 5,000 miles with water-in-fuel indicator 26 illuminated, the software in processor 40 should implement routines 43 and 44. In this example, the value of THRESHOLD input at stage 68 in FIG. 3 would be 5,000 miles. Diagnostic tool 38 is used to access permanent memory means 35 to retrieve the value of WIFCOUNT (i.e., the number of events of water-in-fuel abuse), as well as the existence of a fault code to alert that the 5,000 mile threshold had been exceeded on at least one occasion. Further, diagnostic tool 38 may retrieve an historical chronology of water-in-fuel abuse if, as discussed above, WIFDIST is written to an array and stored in permanent memory means 35 at stage 64 of routine 43.

Once vehicle 5 had been subjected to excessive water-in-fuel abuse, such as chronic or single-event abuse beyond a threshold or a large number of events of water-in-fuel abuse, the fuel injection pump (not shown) associated with vehicle engine 8 is likely to have internal rusting and to fail accordingly. Diagnosing whether permanent memory means 35 contains a fault code or reveals a large number of events of water-in-fuel abuse enables an engine manufacturer to know whether a warranty claim is justified. Diagnostic tool 38 is operatively connected to permanent memory means 35. If diagnostic tool 38 applied to permanent memory means 35 detects the presence of a fault code, reveals an excessive number of events of water-in-fuel abuse, or sets forth an historical chronology of water-in-fuel abuse that is deemed to be excessive, a warranty claim can be denied based on the vehicle operator's neglect of water-in-fuel indicator 26. Because the data characteristic of water-in-fuel abuse (whether fault codes, the number of events of water-in-fuel abuse, or historical values of the duration of water-in-fuel abuse), are permanently written to permanent memory means 35, a diagnostic tool applied to permanent memory means 35 will reveal the abuse regardless of any change in vehicle ownership, thus, the abuse cannot be disguised by changes in vehicle ownership. On the other hand, if diagnostic tool 38 reveals the absence of excessive water-in-fuel abuse, the vehicle operator has not neglected water-in-fuel indicator 26 and warranty coverage is then available.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In reading the claims it is intended that when words such as "a", "an", "at least one", and "at least a portion" are used there is no intention to limit the claims to only one item unless specifically stated to the contrary in the claims. Further, when the language "at least a portion" and/or "a portion" is used, the claims may include a portion and/or the entire items unless specifically stated to the contrary.

What is claimed is:

1. A water-in-fuel abuse detection system comprising:
   a fuel filter for separating an amount of water from a source of fuel;
   means for detecting if said amount of water in said fuel filter attains a certain quantity; and
   means, operatively connected to said means for detecting, for determining a duration that said means for detecting indicates said amount of water equals or exceeds said certain quantity apart from a purging period.

2. The water-in-fuel detection system of claim 1, wherein said duration is measured in terms of distance traversed.

3. The water-in-fuel detection system of claim 1, wherein said duration is measured in terms of time elapsed.

4. The water-in-fuel detection system of claim 1, further comprising means for determining a greatest value of said duration.

5. The water-in-fuel detection system of claim 1, further comprising means for recording if said duration exceeds a threshold.

6. The water-in-fuel detection system of claim 5, further comprising permanent memory means, and wherein said means for recording comprises writing a fault code to said permanent memory means.

7. The water-in-fuel detection system of claim 6, further comprising a diagnostic tool capable of determining if said permanent memory means contains said fault code.

8. A water-in-fuel abuse detection system comprising:
   a fuel filter for separating an amount of water from a source of fuel;
   a sensor for detecting if said amount of water in said fuel filter attains a certain quantity; and
   a software routine, operatively connected to said sensor, for determining a duration that said sensor detects that said amount of water equals or exceeds said certain quantity apart from a purging period.

9. The water-in-fuel detection system of claim 8, wherein said software routine further determines a greatest value of said duration.

10. A method for detecting water-in-fuel abuse comprising:
    providing a fuel filter capable of separating an amount of water from a source of fuel;
    detecting if said amount of water in said fuel filter attains a certain quantity; and
    determining a duration that said amount of water equals or exceeds said certain quantity apart from a purging period.

11. The method for detecting water-in-fuel abuse of claim 10, further comprising determining a greatest value of said duration and writing said greatest value to permanent memory means.

12. The method for detecting water-in-fuel abuse of claim 10 further comprising writing a fault code to permanent memory means if said duration exceeds a threshold.

13. The method for detecting water-in-fuel abuse of claim 12, further comprising using a diagnostic tool to determine if said permanent memory means contains said fault code.

14. A method for determining a warranty claim comprising:
    providing a fuel filter capable of separating an amount of water from a source of fuel;
    detecting if said amount of water in said fuel filter attains a certain quantity;
    determining data characteristic of water-in-fuel abuse apart from automatically purging water;
    writing data to permanent memory means;
    using a diagnostic tool to access said data in said permanent memory means; and
    providing warranty coverage if said data reveals the absence of excessive water-in-fuel abuse.

15. The method for determining a warranty claim of claim 14, wherein said data are one or more durations that said amount of water equals or exceeds said certain quantity.

16. The method for determining a warranty claim of claim 15, wherein said data further include a fault code and said writing step is performed if said one or more durations exceed a threshold that is characteristic of said excessive water-in-fuel abuse.

17. The method for determining a warranty claim of claim 14, wherein said data are the greatest of one or more durations that said amount of water equals or exceeds said certain quantity.

18. The method for determining a warranty claim of claim 14, wherein said fuel filter has a nominal state, said method further comprising:
counting a number of events characterized by detecting that said amount of water equals or exceeds said certain quantity subsequent to said fuel filter existing in said nominal state, wherein said data are said number of events.

* * * * *